United States Patent
Wang et al.

(10) Patent No.: US 12,016,951 B2
(45) Date of Patent: Jun. 25, 2024

(54) EDARAVONE PHARMACEUTICAL COMPOSITION

(71) Applicants: BEIJING TIANTAN HOSPITAL, CAPITAL MEDICAL UNIVERSITY, Beijing (CN); NANJING BAIXINYU PHARMACEUTICAL CO. LTD., Nanjing (CN)

(72) Inventors: Yilong Wang, Beijing (CN); Yongjun Wang, Beijing (CN); Xingquan Zhao, Beijing (CN); Anyuan Zhang, Nanjing (CN)

(73) Assignees: BEIJING TIANTAN HOSPITAL, CAPITAL MEDICAL UNIVERSITY, Beijing (CN); NANJING BAIXINYU PHARMACEUTICAL CO. LTD., Nanjing (CN)

( * ) Notice: Subject to any disclaimer, the term of this patent is extended or adjusted under 35 U.S.C. 154(b) by 877 days.

(21) Appl. No.: 17/049,648

(22) PCT Filed: Dec. 27, 2018

(86) PCT No.: PCT/CN2018/124247
§ 371 (c)(1),
(2) Date: Oct. 22, 2020

(87) PCT Pub. No.: WO2019/205700
PCT Pub. Date: Oct. 31, 2019

(65) Prior Publication Data
US 2021/0244657 A1    Aug. 12, 2021

(30) Foreign Application Priority Data

Apr. 27, 2018  (CN) .......................... 201810392676.8
Jul. 19, 2018   (CN) .......................... 201810797624.9

(51) Int. Cl.
*A61K 9/00*   (2006.01)
*A61K 9/20*   (2006.01)
*A61K 31/4152*   (2006.01)

(52) U.S. Cl.
CPC ............ *A61K 9/006* (2013.01); *A61K 9/2009* (2013.01); *A61K 9/2013* (2013.01); *A61K 9/2018* (2013.01); *A61K 9/2031* (2013.01); *A61K 9/2054* (2013.01); *A61K 9/2059* (2013.01); *A61K 31/4152* (2013.01)

(58) Field of Classification Search
None
See application file for complete search history.

(56) References Cited

U.S. PATENT DOCUMENTS

| | | | |
|---|---|---|---|
| 2007/0286900 A1 | 12/2007 | Herry et al. | |
| 2014/0228420 A1* | 8/2014 | Yoneoka | A61P 21/02 514/404 |
| 2017/0312253 A1 | 11/2017 | Wang et al. | |
| 2020/0297697 A1* | 9/2020 | Wang | A61K 47/26 |

FOREIGN PATENT DOCUMENTS

| | | |
|---|---|---|
| CN | 101953832 | 1/2011 |
| CN | 105616405 | 6/2016 |
| CN | 107773545 | 3/2018 |
| CN | 110693882 | 1/2020 |
| EP | 3505161 | 7/2019 |
| JP | 2002-020290 | 1/2002 |
| JP | 2009-539808 | 11/2009 |
| WO | WO 2013/035712 | 3/2013 |
| WO | WO 2018/040989 | 3/2018 |

OTHER PUBLICATIONS

Karam. American Journal of Hospice and Paliative Medicine, 2015, 33(1), 84-92 (Year: 2015).*
Bushnell. Stroke, 2014, 45, 1545-1588 (Year: 2014).*
Extended European Search Report issued in European Patent Application No. 18916934.5, dated Dec. 17, 2021.
English translation of International Search Report issued in International Patent Application No. PCT/CN2018/124247, dated Mar. 21, 2019.
English translation of Office Communication issued in Japanese Patent Application No. 2020-560232, dated Sep. 28, 2021.
Office Communication issued in Canadian Patent Application No. 3,097,053, dated Oct. 22, 2021.

* cited by examiner

*Primary Examiner* — Noble E Jarrell
(74) *Attorney, Agent, or Firm* — Parker Highlander PLLC

(57) ABSTRACT

Disclosed in the present invention are an edaravone pharmaceutical composition and an application thereof as a sublingual preparation, the pharmaceutical composition containing edaravone or a salt thereof and mannitol. A sublingual administration preparation can avoid the first-pass effect of the liver, and samples feature good stability, convenience of transport and of use, among other advantages.

20 Claims, 2 Drawing Sheets

EDARAVONE PHARMACEUTICAL COMPOSITION

This application is the national phase of International Application No. PCT/CN2018/124247, titled "EDARAVONE PHARMACEUTICAL COMPOSITION", filed on Dec. 27, 2018, which claims the priority of Chinese Patent Application No. 201810392676.8, titled "EDARAVONE PHARMACEUTICAL COMPOSITION", filed on Apr. 27, 2018 with the China National Intellectual Property Administration, and Chinese Patent Application No. 201810797624.9, titled "EDARAVONE PHARMACEUTICAL COMPOSITION", filed on Jul. 19, 2018 with the China National Intellectual Property Administration, which are incorporated herein by reference in entirety.

FIELD

The invention belongs to the field of medical technology and relates to a sublingual edaravone pharmaceutical composition and the use thereof.

BACKGROUND

Edaravone (chemical name: 3-methyl-1-phenyl-2-pyrazoline-5-one) is a cerebral nerve protective agent that has been marketed (Yakugaku Zasshi. 2004, 124(3): 99-111). Studies have shown that edaravone has antioxidant activity, which can significantly improve the symptoms of neurological deficits in cerebral ischemia-reperfusion animals, reduce the infarct size, reduce the degree of brain damage, alleviate cerebral edema, and inhibit lipid peroxidation in damaged brain tissue.

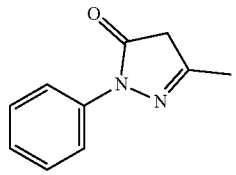

Edaravone
(Molecular formula $C_{10}H_{10}N_2O$, molecular weight 174.20)

Cerebrovascular disease, especially ischemic cerebrovascular disease, is an acute disease, and it needs to be relieved quickly. Therefore, administration by injection is the preferred method of first aid. However, the application of intramuscular injection or intravenous injection is subject to certain medical restrictions due to its tendency to cause pain and irritation at the injection site, and the requirement for operation by medical professionals as well as injection supplies, etc., making it difficult to apply to patients with out-hospital onset.

Sublingual preparations are those directly absorbed by the sublingual mucosa. The sublingual mucosa has a large surface area and strong penetrating ability, and a large number of capillaries under the mucosa gather to the internal jugular vein and directly enter the blood circulation through the superior vena cava. After administration, the drug is quickly absorbed with a rapid onset. The preparations are accurate in quantification and convenient of use, avoiding the first-pass effect of oral drugs. For unexpected cerebrovascular diseases, sublingual preparations, especially sublingual tablets, can greatly improve the convenience of drug administration and the compliance of clinical patients as compared to injections.

However, sublingual pharmaceutical compositions containing edaravone are not easy to prepare. The inventor has found through experiments that many commonly used excipients are not suitable for preparing qualified sublingual preparations, or the performance (stability, release rate, etc.) of the prepared sublingual preparations is not satisfactory.

Therefore, there is still an urgent need for a sublingual pharmaceutical composition containing edaravone with satisfactory stability and/or release rate.

SUMMARY

The object of the present invention is to provide a sublingual pharmaceutical composition containing edaravone or a salt thereof as an active ingredient, which has satisfactory stability and/or release rate.

The inventors have unexpectedly discovered that some commonly used fillers, such as lactose, are not suitable for the formulation of the edaravone sublingual preparations. In the experiment, it was found that the edaravone preparation prepared with lactose as a filler performed poorly in the stability test, causing problems such as color discoloration.

After further experiments, the inventor unexpectedly found that by using fillers excluding those easily cause color changes, such as using mannitol as a filler, in an edaravone pharmaceutical composition, the problems described above can be effectively solved and the edaravone pharmaceutical composition with satisfactory stability and/or release rate is obtained. Based on this finding, the present invention provides a pharmaceutical composition containing edaravone or a salt thereof.

The results of pharmacokinetic data showed that the pharmacokinetic parameters Tmax, Cmax and AUC of the edaravone pharmaceutical composition of the present invention administered sublingually and the edaravone injection administered by intravenous drip are almost the same, and this fully proves that the edaravone pharmaceutical composition of the present invention can completely replace the edaravone injection for use in clinical applications. Meanwhile, sublingual administration improves patient compliance and convenience of drug administration, greatly reducing emergency time and medical costs.

In the first aspect, the present invention provides a pharmaceutical composition comprising edaravone or a salt thereof as an active ingredient, a filler, a binder, and a disintegrant.

In one embodiment, the pharmaceutical composition is a sublingual preparation, for example, it may be in the form of tablets, films, flakes, gums, drops, powders or gels, etc., in particular, it may be sublingual tablets.

In another embodiment, the pharmaceutical composition does not comprise 2-camphanol, preferably does not comprise active ingredients other than edaravone or a salt thereof.

In one embodiment, the filler is not lactose, starch or microcrystalline cellulose, preferably the filler comprises mannitol, more preferably the filler is mannitol.

In one embodiment, in the pharmaceutical composition of the present invention, the mass ratio of edaravone or a salt thereof to the filler is 1:10 to 2:1, preferably 1:5 to 2:1, wherein when the edaravone salt is used as an active ingredient, the amount thereof is calculated based on edaravone (the same below).

In one embodiment, the filler accounts for 25% to 90%, 30% to 80%, 35% to 75%, 40% to 70%, 40% to 50% or 50% to 60% by mass of the pharmaceutical composition.

In one embodiment, the binder is not copovidone, preferably the binder comprises hydroxypropyl methylcellulose, more preferably the binder is hydroxypropyl methylcellulose.

In another embodiment, the disintegrant comprises at least one selected from the group consisting of croscarmellose sodium and crospovidone, preferably the disintegrant comprises crospovidone, more preferably the disintegrant is crospovidone.

In another embodiment, the pharmaceutical composition further comprises a lubricant, for example the lubricant comprises magnesium stearate, preferably the lubricant is magnesium stearate.

In another embodiment, the pharmaceutical composition further comprises a glidant, for example the glidant comprises silica, preferably the glidant is silica.

In another embodiment, in the pharmaceutical composition of the present invention, the mass ratio of the filler:the binder:the disintegrant is (10 to 70):(0.5 to 15):(0.5 to 20) or (15 to 50):(1 to 8):(1 to 10).

In another embodiment, the pharmaceutical composition exists in a unit dosage form, wherein each unit dosage form of the pharmaceutical composition may contain 5 mg to 100 mg of edaravone or a salt thereof, or 10 mg to 80 mg, or 15 mg, 20 mg, 25 mg, 30 mg, 40 mg, 50 mg, 60 mg, 70 mg, 75 mg, 80 mg, 90 mg, 100 mg, or a value between any two of the above. When the edaravone salt is used as an active ingredient, the amount thereof is calculated based on edaravone (the same below).

In one embodiment, for sublingual preparations, a blood concentration of the edaravone reaches 10 to 10,000 ng/mL within 0.1 to 24 hours after sublingual administration to a patient in a unit dosage form.

In another embodiment, the pharmaceutical composition may also optionally comprise other pharmaceutically acceptable carriers such as lubricants, glidants, and/or flavoring agents in addition to the active ingredients, fillers, binders and disintegrants. In particular, in addition to the specific ingredients listed above, other ingredients that may function as fillers, binders, disintegrants, glidants, and/or lubricants can also be comprised, provided that their addition does not significantly affect the stability and/or release rate of the pharmaceutical composition of the present invention. Those skilled in the art can make selections according to actual needs. For example, suitable binders or excipients may also include, but are not limited to, cyclodextrin, ethyl cellulose, microcrystalline cellulose, dicalcium phosphate, calcium carbonate, silica, methyl cellulose, carboxymethyl cellulose, hydroxymethyl cellulose, alginate, gelatin, guar gum, tragacanth gum, gum arabic, polyacrylic acid, polymethacrylic acid, polysilicic acid and salts thereof, polylactic acid, polymaleic acid, polyvinyl alcohol, polyethylene glycol, polyvinylpyrrolidone, non-ionic block copolymer, carbomer, polycarbophil, polysorbate, water-soluble starch, and the like, or a combination thereof. Suitable lubricants can be selected from the group consisting of stearic acid, magnesium stearate, micronized silica gel, sodium stearyl fumarate, or a combination thereof. Suitable disintegrants can be selected from the group consisting of sodium carboxymethyl starch, croscarmellose sodium, crospovidone, low-substituted hydroxypropyl cellulose, or a combination thereof. Suitable flavoring agents can be selected from the group consisting of citric acid, acesulfame, aspartame, sucralose, and the like, or a combination thereof.

In another aspect, provided in the present invention are a method for the treatment and/or prevention of cerebrovascular disease and/or amyotrophic lateral sclerosis using the pharmaceutical composition, the pharmaceutical composition for use in the treatment and/or prevention of cerebrovascular disease and/or amyotrophic lateral sclerosis, and use of the pharmaceutical composition in the preparation of a medicament for the treatment and/or prevention of cerebrovascular disease and/or amyotrophic lateral sclerosis. In some embodiments, the cerebrovascular disease is ischemic cerebrovascular disease, such as stroke.

In another aspect, the pharmaceutical composition of the present invention can be prepared by mixing the active ingredient edaravone or a salt thereof with a suitable pharmaceutically acceptable carrier. In particular, for sublingual preparations, the following preparation methods can be adopted: mixing edaravone or a salt thereof with a suitable pharmaceutically acceptable carrier, and compressing into tablets.

DETAILED DESCRIPTION

Figure 1:
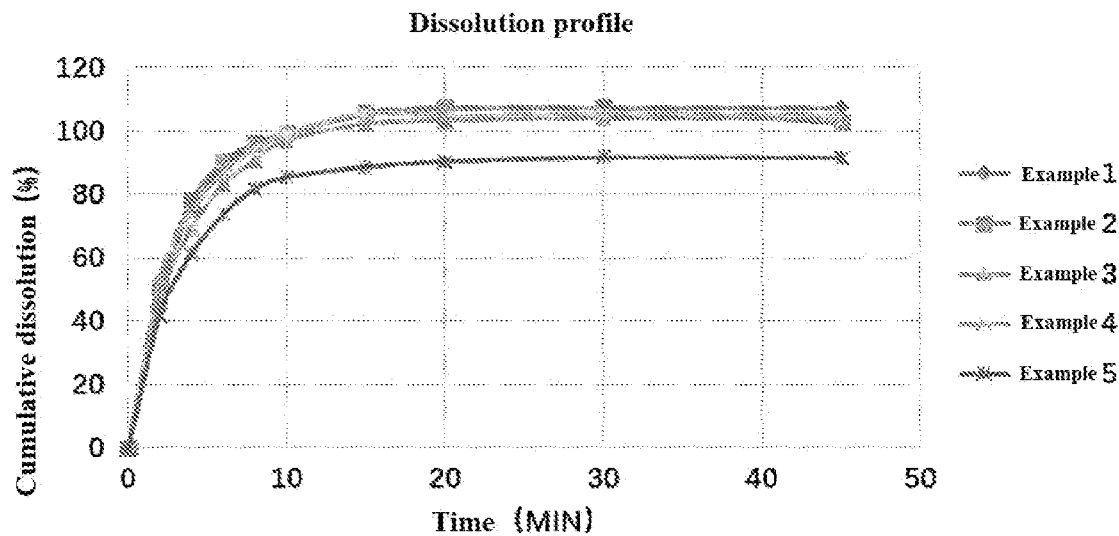
FIG. 1 is the dissolution profile of the sublingual tablets prepared according to Examples 1 to 5.

The present invention discloses an edaravone pharmaceutical composition, especially in a form of sublingual preparations. Those skilled in the art can achieve this by using the content of the present invention for reference, combining the principles of pharmacy, and appropriately improving the process parameters or the formula ratio. It should be particularly pointed out that all similar substitutions and modifications are obvious to those skilled in the art, and they are all deemed to be included in the scope of the present invention. The applications of the present invention have been well described through the examples, and relevant personnel can make appropriate changes, alterations or combinations to the methods and applications described herein without departing from the content, spirit and scope of the present invention to achieve and apply the present invention.

The following examples are used to further illustrate the present invention, but they are not meant to limit the protection scope of the present invention in any way.

The reagents and instruments used in the examples of the present disclosure are all commercially available, and the bulk drugs and various excipients/additives, such as edaravone (Jiangsu Tiansheng Pharmaceutical Co., Ltd), lactose (FLOWLAC 100), microcrystalline cellulose (CEOLUS PH302), mannitol (Pearlitol 200SD), copovidone (PLASDONE S-630), hydroxypropyl methylcellulose (SH-E5), croscarmellose sodium (AcDi Sol), crospovidone (POLYPLASDONE XL-10), starch (tapioca starch), silica (Huzhou Zhanwang Pharmaceutical Co., Ltd.), magnesium stearate (Anhui Sunhere Pharmaceutical Excipients Co., Ltd.), are all in compliance with pharmaceutical standards.

Example 1

| Material Name | Dosage per tabelet (mg) | Role |
|---|---|---|
| Edaravone | 30 | Active ingredient |
| Lactose | 41.2 | Filler |
| Hydroxypropyl methylcellulose | 4 | Binder |
| Croscarmellose sodium | 4 | Disintegrant |
| Magnesium stearate | 0.8 | Lubricant |

Preparation method: Edaravone, lactose, hydroxypropyl methylcellulose, croscarmellose sodium, and magnesium stearate were mixed uniformly according to the formula ratio, and the mixture was compressed into tablets.

Example 2

| Material Name | Dosage per tabelet (mg) | Role |
|---|---|---|
| Edaravone | 30 | Active ingredient |
| Starch | 41.2 | Filler |
| Hydroxypropyl methylcellulose | 4 | Binder |
| Croscarmellose sodium | 4 | Disintegrant |
| Magnesium stearate | 0.8 | Lubricant |

Preparation method: Edaravone, starch, hydroxypropyl methylcellulose, croscarmellose sodium, and magnesium stearate were mixed uniformly according to the formula ratio, and the mixture was compressed into tablets.

Example 3

| Material Name | Dosage per tabelet (mg) | Role |
|---|---|---|
| Edaravone | 30 | Active ingredient |
| Microcrystalline cellulose | 41.2 | Filler |
| Hydroxypropyl methylcellulose | 4 | Binder |
| Croscarmellose sodium | 4 | Disintegrant |
| Magnesium stearate | 0.8 | Lubricant |

Preparation method: Edaravone, microcrystalline cellulose, hydroxypropyl methylcellulose, croscarmellose sodium, and magnesium stearate were mixed uniformly according to the formula ratio, and the mixture was compressed into tablets.

Example 4

| Material Name | Dosage per tabelet (mg) | Role |
|---|---|---|
| Edaravone | 30 | Active ingredient |
| Mannitol | 41.2 | Filler |
| Hydroxypropyl methylcellulose | 4 | Binder |
| Croscarmellose sodium | 4 | Disintegrant |
| Magnesium stearate | 0.8 | Lubricant |

Preparation method: Edaravone, mannitol, hydroxypropyl methylcellulose, croscarmellose sodium, and magnesium stearate were mixed uniformly according to the formula ratio, and the mixture was compressed into tablets.

Example 5

| Material Name | Dosage per tabelet (mg) | Role |
|---|---|---|
| Edaravone | 30 | Active ingredient |
| Lactose | 41.2 | Filler |
| Copovidone | 4 | Binder |
| Croscarmellose sodium | 4 | Disintegrant |
| Magnesium stearate | 0.8 | Lubricant |

Preparation method: Edaravone, lactose, copovidone, croscarmellose sodium, and magnesium stearate were mixed uniformly according to the formula ratio, and the mixture was compressed into tablets.

Example 6

| Material Name | Dosage per tabelet (mg) | Role |
|---|---|---|
| Edaravone | 30 | Active ingredient |
| Microcrystalline cellulose | 41.2 | Filler |
| Copovidone | 4 | Binder |
| Croscarmellose sodium | 4 | Disintegrant |
| Magnesium stearate | 0.8 | Lubricant |

Preparation method: Edaravone, microcrystalline cellulose, copovidone, croscarmellose sodium, and magnesium stearate were mixed uniformly according to the formula ratio, and the mixture was compressed into tablets.

Example 7

| Material Name | Dosage per tabelet (mg) | Role |
|---|---|---|
| Edaravone | 30 | Active ingredient |
| Mannitol | 41.2 | Filler |
| Copovidone | 4 | Binder |
| Croscarmellose sodium | 4 | Disintegrant |
| Magnesium stearate | 0.8 | Lubricant |

Preparation method: edaravone, mannitol, copovidone, croscarmellose sodium, and magnesium stearate were mixed uniformly according to the formula ratio, and the mixture was compressed into tablets.

Example 8

| Material Name | Dosage per tabelet (mg) | Role |
|---|---|---|
| Edaravone | 30 | Active ingredient |
| Lactose | 41.2 | Filler |
| Hydroxypropyl methylcellulose | 4 | Binder |
| Crospovidone | 4 | Disintegrant |
| Magnesium stearate | 0.8 | Lubricant |

Preparation method: Edaravone, lactose, hydroxypropyl methylcellulose, crospovidone, and magnesium stearate were mixed uniformly according to the formula ratio, and the mixture was compressed into tablets.

Example 9

| Material Name | Dosage per tabelet (mg) | Role |
|---|---|---|
| Edaravone | 30 | Active ingredient |
| Microcrystalline cellulose | 41.2 | Filler |
| Hydroxypropyl methylcellulose | 4 | Binder |
| Crospovidone | 4 | Disintegrant |
| Magnesium stearate | 0.8 | Lubricant |

Preparation method: Edaravone, microcrystalline cellulose, hydroxypropyl methylcellulose, crospovidone, and magnesium stearate were mixed uniformly according to the formula ratio, and the mixture was compressed into tablets.

Example 10

| Material Name | Dosage per tabelet (mg) | Role |
|---|---|---|
| Edaravone | 30 | Active ingredient |
| Mannitol | 41.2 | Filler |
| Hydroxypropyl methylcellulose | 4 | Binder |
| Crospovidone | 4 | Disintegrant |
| Magnesium stearate | 0.8 | Lubricant |

Preparation method: edaravone, mannitol, hydroxypropyl methylcellulose, crospovidone and magnesium stearate were mixed uniformly according to the formula ratio, and the mixture was compressed into tablets.

Example 11

| Material Name | Dosage per tabelet (mg) | Role |
|---|---|---|
| Edaravone | 30 | Active ingredient |
| Mannitol | 40.4 | Filler |
| Hydroxypropyl methylcellulose | 4 | Binder |
| Crospovidone | 4 | Disintegrant |
| Silica | 0.8 | Glidant |
| Magnesium stearate | 0.8 | Lubricant |

Preparation method: Edaravone, mannitol, hydroxypropyl methylcellulose, crospovidone, silica, and magnesium stearate were mixed uniformly according to the formula ratio, and the mixture was compressed into tablets.

Example 12

| Material Name | Dosage per tabelet (mg) | Role |
|---|---|---|
| Edaravone | 30 | Active ingredient |
| Mannitol | 15 | Filler |
| Hydroxypropyl methylcellulose | 2 | Binder |
| Crospovidone | 5 | Disintegrant |
| Silica | 0.5 | Glidant |
| Magnesium stearate | 0.5 | Lubricant |

Preparation method: Edaravone, mannitol, hydroxypropyl methylcellulose, crospovidone, silica, and magnesium stearate were mixed uniformly according to the formula ratio, and the mixture was compressed into tablets.

Example 13

| Material Name | Dosage per tabelet (mg) | Role |
|---|---|---|
| Edaravone | 30 | Active ingredient |
| Mannitol | 30.2 | Filler |
| Hydroxypropyl methylcellulose | 1.4 | Binder |
| Crospovidone | 7 | Disintegrant |
| Silica | 0.7 | Glidant |
| Magnesium stearate | 0.7 | Lubricant |

Preparation method: Edaravone, mannitol, hydroxypropyl methylcellulose, crospovidone, silica, and magnesium stearate were mixed uniformly according to the formula ratio, and the mixture was compressed into tablets.

Example 14

| Material Name | Dosage per tabelet (mg) | Role |
|---|---|---|
| Edaravone | 30 | Active ingredient |
| Mannitol | 186 | Filler |
| Hydroxypropyl methylcellulose | 10 | Binder |
| Crospovidone | 20 | Disintegrant |
| Silica | 2 | Glidant |
| Magnesium stearate | 2 | Lubricant |

Preparation method: Edaravone, mannitol, hydroxypropyl methylcellulose, crospovidone, silica, and magnesium stearate were mixed uniformly according to the formula ratio, and the mixture was compressed into tablets.

Example 15

Stability test results: An appropriate amount of samples from Examples 1-14 were packaged in a simulated market packaging, and placed at a temperature of 40° C. or 60° C. for 10 days or 30 days for sampling. The characteristics, edaravone content, and related substances were determined and the results were shown in the following table:

| Examples | Placing Conditions | Characteristics | Content (%) | Related Substances (%) |
|---|---|---|---|---|
| Example 1 | 0 day | White to off-white tablets | 99.83 | 0.09 |
| | 40° C., 10 days | Light yellow tablets | 99.64 | 0.13 |
| | 60° C., 10 days | Light yellow tablets | 99.57 | 0.31 |
| | 40° C., 30 days | Light yellow tablets | 98.48 | 0.76 |
| | 60° C., 30 days | Light yellow tablets | 98.85 | 0.98 |
| Example 2 | 0 day | White to off-white tablets | 99.62 | 0.07 |
| | 40° C., 10 days | Light yellow tablets | 99.75 | 0.21 |
| | 60° C., 10 days | Light yellow tablets | 99.82 | 0.36 |
| | 40° C., 30 days | Light yellow tablets | 98.64 | 0.84 |

| Examples | Placing Conditions | Characteristics | Content (%) | Related Substances (%) |
|---|---|---|---|---|
| | 60° C., 30 days | Light yellow tablets | 98.34 | 0.94 |
| Example 3 | 0 day | White to off-white tablets | 100.02 | 0.02 |
| | 40° C., 10 days | Light yellow tablets | 100.04 | 0.16 |
| | 60° C., 10 days | Light yellow tablets | 99.38 | 0.38 |
| | 40° C., 30 days | Light yellow tablets | 98.56 | 0.72 |
| | 60° C., 30 days | Light yellow tablets | 98.98 | 1.06 |
| Example 4 | 0 day | White to off-white tablets | 99.26 | 0.01 |
| | 40° C., 10 days | White to off-white tablets | 99.75 | 0.05 |
| | 60° C., 10 days | White to off-white tablets | 99.21 | 0.10 |
| | 40° C., 30 days | White to off-white tablets | 99.25 | 0.43 |
| | 60° C., 30 days | White to off-white tablets | 98.45 | 0.77 |
| Example 5 | 0 day | White to off-white tablets | 99.88 | 0.06 |
| | 40° C., 10 days | Light yellow tablets | 99.27 | 0.23 |
| | 60° C., 10 days | Light yellow tablets | 99.36 | 0.51 |
| | 40° C., 30 days | Light yellow tablets | 98.25 | 1.01 |
| | 60° C., 30 days | Light yellow tablets | 97.34 | 1.12 |
| Example 6 | 0 day | White to off-white tablets | 98.24 | 0.10 |
| | 40° C., 10 days | Light yellow tablets | 98.65 | 0.21 |
| | 60° C., 10 days | Light yellow tablets | 97.15 | 0.54 |
| | 40° C., 30 days | Light yellow tablets | 98.12 | 1.02 |
| | 60° C., 30 days | Light yellow tablets | 97.86 | 1.12 |
| Example 7 | 0 day | White to off-white tablets | 98.65 | 0.02 |
| | 40° C., 10 days | White to off-white tablets | 100.42 | 0.08 |
| | 60° C., 10 days | White to off-white tablets | 99.56 | 0.10 |
| | 40° C., 30 days | White to off-white tablets | 98.89 | 0.43 |
| | 60° C., 30 days | White to off-white tablets | 98.56 | 0.57 |
| Example 8 | 0 day | White to off-white tablets | 100.14 | 0.05 |
| | 40° C., 10 days | Light yellow tablets | 100.23 | 0.13 |
| | 60° C., 10 days | Light yellow tablets | 100.10 | 0.45 |
| | 40° C., 30 days | Light yellow tablets | 98.26 | 0.78 |
| | 60° C., 30 days | Light yellow tablets | 98.84 | 0.95 |
| Example 9 | 0 day | White to off-white tablets | 99.58 | 0.08 |
| | 40° C., 10 days | Light yellow tablets | 99.56 | 0.26 |
| | 60° C., 10 days | Light yellow tablets | 99.84 | 0.46 |
| | 40° C., 30 days | Light yellow tablets | 98.56 | 0.98 |
| | 60° C., 30 days | Light yellow tablets | 98.87 | 1.12 |
| Example 10 | 0 day | White to off-white tablets | 99.52 | 0.01 |
| | 40° C., 10 days | White to off-white tablets | 99.45 | 0.04 |
| | 60° C., 10 days | White to off-white tablets | 99.36 | 0.12 |
| | 40° C., 30 days | White to off-white tablets | 98.78 | 0.42 |
| | 60° C., 30 days | White to off-white tablets | 98.85 | 0.63 |
| Example 11 | 0 day | White to off-white tablets | 99.18 | 0.02 |
| | 40° C., 10 days | White to off-white tablets | 99.45 | 0.08 |
| | 60° C., 10 days | White to off-white tablets | 99.25 | 0.16 |
| | 40° C., 30 days | White to off-white tablets | 98.47 | 0.35 |
| | 60° C., 30 days | White to off-white tablets | 98.36 | 0.75 |
| Example 12 | 0 day | White to off-white tablets | 99.58 | 0 |
| | 40° C., 10 days | White to off-white tablets | 99.76 | 0.09 |
| | 60° C., 10 days | White to off-white tablets | 99.85 | 0.21 |
| | 40° C., 30 days | White to off-white tablets | 98.37 | 0.31 |
| | 60° C., 30 days | White to off-white tablets | 98.21 | 0.76 |
| Example 13 | 0 day | White to off-white tablets | 100.49 | 0 |
| | 40° C., 10 days | White to off-white tablets | 99.94 | 0.07 |
| | 60° C., 10 days | White to off-white tablets | 98.26 | 0.18 |
| | 40° C., 30 days | White to off-white tablets | 98.90 | 0.27 |
| | 60° C., 30 days | White to off-white tablets | 98.40 | 0.81 |
| Example 14 | 0 day | White to off-white tablets | 99.86 | 0.02 |
| | 40° C., 10 days | White to off-white tablets | 99.78 | 0.06 |
| | 60° C., 10 days | White to off-white tablets | 99.85 | 0.15 |
| | 40° C., 30 days | White to off-white tablets | 98.57 | 0.24 |
| | 60° C., 30 days | White to off-white tablets | 98.46 | 0.91 |

According to the above table, the test results of Examples 1-14 showed that after being placed at a higher temperature for 30 days, the content of the active substance edaravone in all Examples 1-14 remained above 97%, which was satisfactory; the content of the active substance edaravone in most of the examples was kept above 98% except for a few examples (Examples 5 and 6). However, the inventors unexpectedly found that when lactose, starch or microcrystalline cellulose was selected as the filler in Examples 1-3, 5-6, and 8-9, color changes occurred on the appearance of the tablets when the tablets were placed at a higher temperature. On the contrary, in Examples 4, 7, and 10-14, when mannitol was used as the filler, the tablets maintained a high content of active ingredients and produced a very small amount of related substances during being placed at a higher temperature. Moreover, the properties were unchanged, all remaining white to off-white tablets, and the stability performance was particularly excellent.

Example 16

Figure 2:
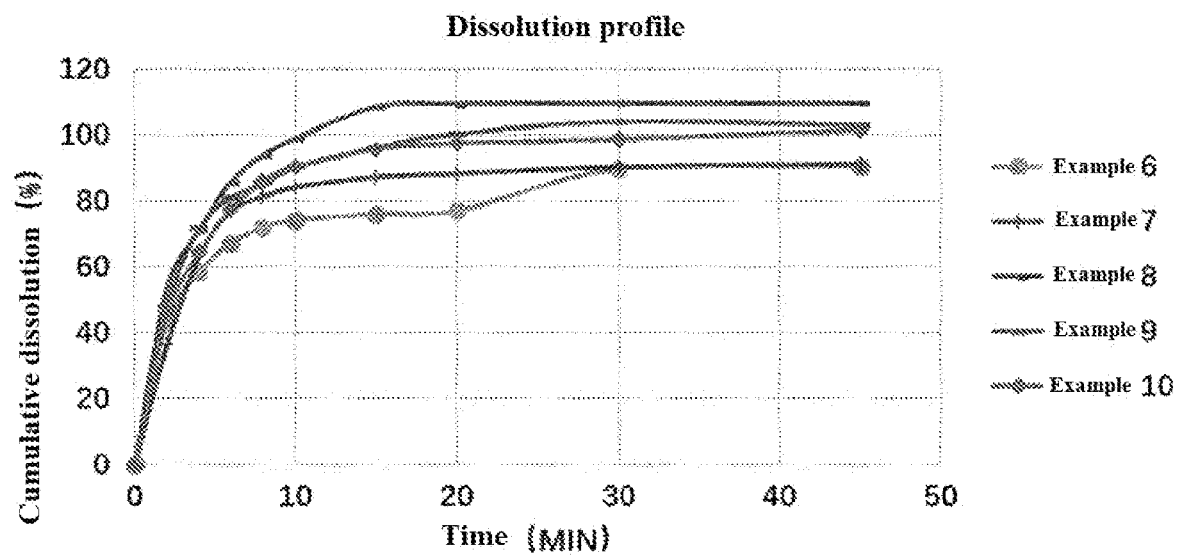
FIG. 2 is the dissolution profile of the sublingual tablets prepared according to Examples 6 to 10.
Figure 3:
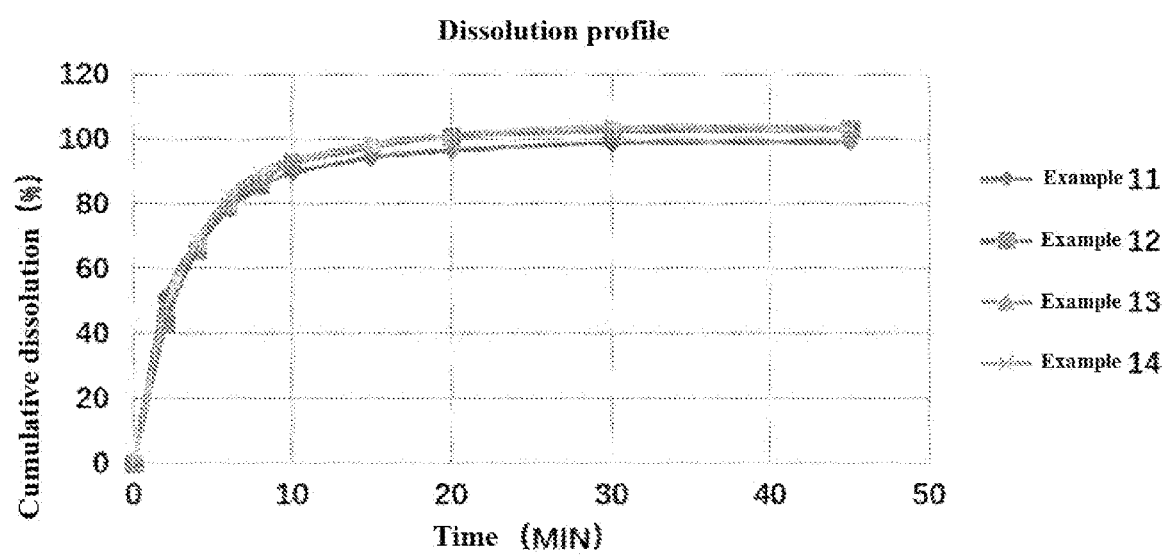
FIG. 3 is the dissolution profile of the sublingual tablets prepared according to Examples 11 to 14.

Test method for determination of dissolution: According to the determination method of the dissolution and release (Chinese Pharmacopoeia 2015, volume IV, 0931, second method), 900 ml of water was functioned as a dissolution medium, and the rotating speed was 50 rpm. Operations were performed according to said method. Samples were taken at different time points, filtered via a 0.8 μm filter membrane, and the subsequent filtrates were taken as the test solution; 20 mmol/L ammonium acetate/acetonitrile (80:20) was added to an appropriate amount of reference substance edaravone, and the edaravone was dissolved and diluted to approximately 0.02 mg/ml for later use. The UV absorbance of the test solution was measured under the condition of 254 nm, and the dissolution rate of the samples was calculated. The results were shown in FIGS. 1, 2, and 3. The dissolution rate of examples 5, 6, and 7 which contains the adhesive copovidone was slower; the formulations of other examples had better dissolution results.

Example 17

Study on Bridging PK of Edaravone Sublingual Tablets and Injections:
Materials and Methods Experimental animals: Beagle dogs, male, weighing 8-10 kg; available from Beijing Marshall Biotechnology Co., Ltd.; certificate No. 11400600012054; license No. SOCK (Beijing) 2016-0001.

Food and water supply: Animals were fasted for 12 hours before the test, and provided food 4 hours after administration. Animals received water ad libitum throughout the experiment. Abnormal reactions in animals were observed and recorded during drug administration and sample collection.

Test drugs: Edaravone injection: specification: 10 mg/5 mL (Nanjing Simcere Pharmaceutical Co., Ltd.); sublingual tablets prepared according to the formula ratio of Example 5 (specification: 30 mg/tablet, tablet weight: 80 mg); sublingual tablets prepared according to the formula ratio of Example 7 (specification: 30 mg/tablet, tablet weight: 80 mg); sublingual tablets prepared according to the formula ratio of Example 13 (specification: 30 mg/tablet, tablet weight: 70 mg); sublingual tablets prepared according to the formula ratio of Example 14 (specification: 30 mg/tablet, tablet weight: 250 mg).

Methods: The dogs were weighed on the day of the experiment, and the body weight of each dog was recorded for dripping or sublingual administration and calculation of related pharmacokinetic parameters.

Group 1: Dripping administration of edaravone injection (N=2)

Dosage for administration: 12 mL, a total of 24 mg edaravone was administered.

The dogs were administered by intravenous dripping and dripping was ended after 12 minutes. The initiation time of dripping was regarded as the time point of 0 min, and then the whole blood was collected at time points of 5 min, 12 min, 30 min, 45 min as well as 1, 1.5, 2, 3, 4, 6, 8, 10, and 24 h.

Group 2: Sublingual administration of one sublingual tablet of Example 5 (N=3).

The Beagle dogs were administered sublingually by inserting the tablet under the tongue of the dogs at a dose of 1 tablet/dog with their mouth kept fixed for 12 minutes to prevent the tablet from falling out. Since involuntary saliva secretion and swallowing affect the efficacy of sublingual administration, their mouth needs to be fixed for 12 minutes. The time when the tablet was placed under the tongue was regarded as the time point of 0 min, and then the whole blood was collected at time points of 5 min, 12 min, 30 min, 45 min as well as 1, 1.5, 2, 3, 4, 6, 8, 10, and 24 h.

Group 3: Sublingual administration of one sublingual tablet of Example 7 (N=3).

The Beagle dogs were administered sublingually by inserting the tablet under the tongue of the dogs at a dose of 1 tablet/dog with their mouth kept fixed for 12 minutes to prevent the tablet from falling out. Since involuntary saliva secretion and swallowing affect the efficacy of sublingual administration, their mouth needs to be fixed for 12 minutes. The time when the tablet was placed under the tongue was regarded as the time point of 0 min, and then the whole blood was collected at time points of 5 min, 12 min, 30 min, 45 min as well as 1, 1.5, 2, 3, 4, 6, 8, 10, and 24 h.

Group 4: Sublingual administration of one sublingual tablet of Example 13 (N=3).

The Beagle dogs were administered sublingually by inserting the tablet under the tongue of the dogs at a dose of 1 tablet/dog with their mouth kept fixed for 12 minutes to prevent the tablet from falling out. Since involuntary saliva secretion and swallowing affect the efficacy of sublingual administration, their mouth needs to be fixed for 12 minutes. The time when the tablet was placed under the tongue was regarded as the time point of 0 min, and then the whole blood was collected at time points of 5 min, 12 min, 30 min, 45 min as well as 1, 1.5, 2, 3, 4, 6, 8, 10, and 24 h.

Group 5: Sublingual administration of one sublingual tablet of Example 14 (N=3).

The Beagle dogs were administered sublingually by inserting the tablet under the tongue of the dogs at a dose of 1 tablet/dog with their mouth kept fixed for 12 minutes to prevent the tablet from falling out. Since involuntary saliva secretion and swallowing affect the efficacy of sublingual administration, their mouth needs to be fixed for 12 minutes. The time when the tablet was placed under the tongue was regarded as the time point of 0 min, and then the whole blood was collected at time points of 5 min, 12 min, 30 min, 45 min as well as 1, 1.5, 2, 3, 4, 6, 8, 10, and 24 h.

Experimental results: Each average pharmacokinetic parameter of edaravone in plasma after intravenous dripping of edaravone injection and sublingual administration of edaravone sublingual tablets in Beagle dogs.

|  | Intravenous injection | Example 5 | Example 7 | Example 13 | Example 14 |
|---|---|---|---|---|---|
| $T_{max}$ (h) | 0.50 | 0.75 | 0.67 | 0.63 | 0.50 |
| $C_{max}$ (ng/mL) | 7195 | 5230 | 6029 | 8380 | 9580 |
| $AUC_{0-24\,h}$ (h*ng/ml) | 12060 | 8115 | 9218 | 15693 | 12281 |
| $AUC_{0-24\,h}$/dose (ng·h·kg·mL$^{-1}$·mg$^{-1}$) | 3934 | 2551 | 2880 | 4939 | 3934 |
| $MRT_{last}$ (h) | 2.87 | 3.39 | 3.25 | 3.18 | 3.51 |
| F (%) | / | 64 | 73 | 125.5 | 100.0 |

The results of the PK bridging of the administration of sublingual tablets and injections for Beagle dogs showed that, for the edaravone sublingual preparations in Example 13 and in Example 14, edaravone was almost completely absorbed, meeting the conditions for sublingual administration. Edaravone sublingual tablets have advantages such as good pharmacokinetic properties, high bioavailability and convenient of use.

The invention claimed is:

1. A sublingual pharmaceutical composition comprising edaravone or a salt thereof as a sole active ingredient, a filler, a binder and a disintegrant;
    wherein the filler comprises mannitol but not comprises lactose;
    wherein the binder comprises hydroxypropyl methylcellulose but does not comprises copovidone; and
    wherein the disintegrant comprises at least one agent selected from the group consisting of croscarmellose sodium and crospovidone.

2. The sublingual pharmaceutical composition according to claim 1, wherein the pharmaceutical composition is a sublingual tablet.

3. The sublingual pharmaceutical composition according to claim 1, wherein the filler is mannitol.

4. The sublingual pharmaceutical composition according to claim 1, wherein the filler accounts for 25% to 90% by mass of the pharmaceutical composition.

5. The sublingual pharmaceutical composition according to claim 1, wherein the binder is hydroxypropyl methylcellulose.

6. The sublingual pharmaceutical composition according to claim 1, wherein the disintegrant comprises crospovidone.

7. The sublingual pharmaceutical composition according to claim 1, wherein the pharmaceutical composition further comprises a lubricant.

8. The sublingual pharmaceutical composition according to claim 1, wherein the pharmaceutical composition further comprises a glidant.

9. The sublingual pharmaceutical composition according to claim 1, wherein a blood concentration of the edaravone reaches 10 to 10,000 ng/mL within 0.1 to 24 hours after sublingual administration to a patient in a unit dosage form.

10. A method of treating cerebrovascular disease or amyotrophic lateral sclerosis in a subject in need thereof, comprising administering to the subject a therapeutically effective amount of the sublingual pharmaceutical composition according to claim 1.

11. The method according to claim 10, wherein the cerebrovascular disease is ischemic encephalopathy.

12. The sublingual pharmaceutical composition according to claim 4, wherein the filler accounts for 30% to 80% by mass of the pharmaceutical composition.

13. The sublingual pharmaceutical composition according to claim 4, wherein the filler accounts for 35% to 75% by mass of the pharmaceutical composition.

14. The sublingual pharmaceutical composition according to claim 4, wherein the filler accounts for 40% to 70% by mass of the pharmaceutical composition.

15. The sublingual pharmaceutical composition according to claim 6, wherein the disintegrant is crospovidone.

16. The sublingual pharmaceutical composition according to claim 7, wherein the lubricant comprises magnesium stearate.

17. The sublingual pharmaceutical composition according to claim 7, wherein the lubricant is magnesium stearate.

18. The sublingual pharmaceutical composition according to claim 8, wherein the glidant comprises silica.

19. The sublingual pharmaceutical composition according to claim 8, wherein the glidant is silica.

20. The method according to claim 10, wherein the cerebrovascular disease is stroke.

* * * * *